United States Patent
Wang et al.

(10) Patent No.: US 9,510,964 B2
(45) Date of Patent: Dec. 6, 2016

(54) STENT CRIMPING TOOL INSERT, SYSTEM, AND METHOD

(71) Applicant: Abbott Cardiovascular Systems Inc., Santa Clara, CA (US)

(72) Inventors: Karen J. Wang, Cupertino, CA (US);
Edward P. Garcia, Dublin, CA (US);
Manish Gada, Santa Clara, CA (US);
Marc Schraner, Pacifica, CA (US);
Michael Green, Pleasanton, CA (US);
Stan Lam, Pleasanton, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

(21) Appl. No.: 14/819,228

(22) Filed: Aug. 5, 2015

(65) Prior Publication Data

US 2015/0359650 A1    Dec. 17, 2015

Related U.S. Application Data

(62) Division of application No. 13/840,185, filed on Mar. 15, 2013, now Pat. No. 9,125,763.

(51) Int. Cl.
| | |
|---|---|
| *B21D 37/18* | (2006.01) |
| *A61F 2/958* | (2013.01) |
| *B21D 41/04* | (2006.01) |
| *B23P 17/04* | (2006.01) |
| *A61F 2/06* | (2013.01) |
| *A61F 2/95* | (2013.01) |

(52) U.S. Cl.
CPC .................. *A61F 2/958* (2013.01); *A61F 2/06* (2013.01); *A61F 2/95* (2013.01); *B21D 37/18* (2013.01); *B21D 41/04* (2013.01); *B23P 17/04* (2013.01); *A61F 2002/9522* (2013.01)

(58) Field of Classification Search
CPC .............. A61F 2/06; A61F 2/84; A61F 2/958; A61F 2/95; A61F 2002/9522; B21D 37/18; B21D 41/04; B23P 17/04
USPC ........................................ 72/44, 54, 402, 463
See application file for complete search history.

(56) References Cited

U.S. PATENT DOCUMENTS

| | | | | |
|---|---|---|---|---|
| 7,284,401 | B2* | 10/2007 | Larson | A61F 2/95 72/402 |
| 9,125,763 | B2* | 9/2015 | Wang | A61F 2/95 |
| 2008/0028594 | A1 | 2/2008 | Lafont et al. | |
| 2008/0127707 | A1* | 6/2008 | Kokish | A61F 2/95 72/402 |
| 2009/0088829 | A1* | 4/2009 | Wang | A61F 2/958 623/1.11 |
| 2009/0131920 | A1* | 5/2009 | Moreno | A61F 2/95 606/1 |
| 2010/0036478 | A1* | 2/2010 | Wang | A61L 31/06 623/1.15 |

(Continued)

FOREIGN PATENT DOCUMENTS

| | | |
|---|---|---|
| CN | 101175454 A | 5/2008 |
| WO | WO 2012/150290 A1 | 11/2012 |

*Primary Examiner* — David B Jones
(74) *Attorney, Agent, or Firm* — Squire Patton Boggs (US) LLP

(57) ABSTRACT

A stent crimping tool insert comprises a core body configured for insertion into and removal from within a crimping chamber of a stent crimping tool. The core body has a core surface configured to withstand a compressive force without a reduction in diameter of the core surface.

7 Claims, 7 Drawing Sheets

(56) References Cited

U.S. PATENT DOCUMENTS

2012/0010693 A1\* 1/2012 Van Sciver ............. A61F 2/958
623/1.11

\* cited by examiner

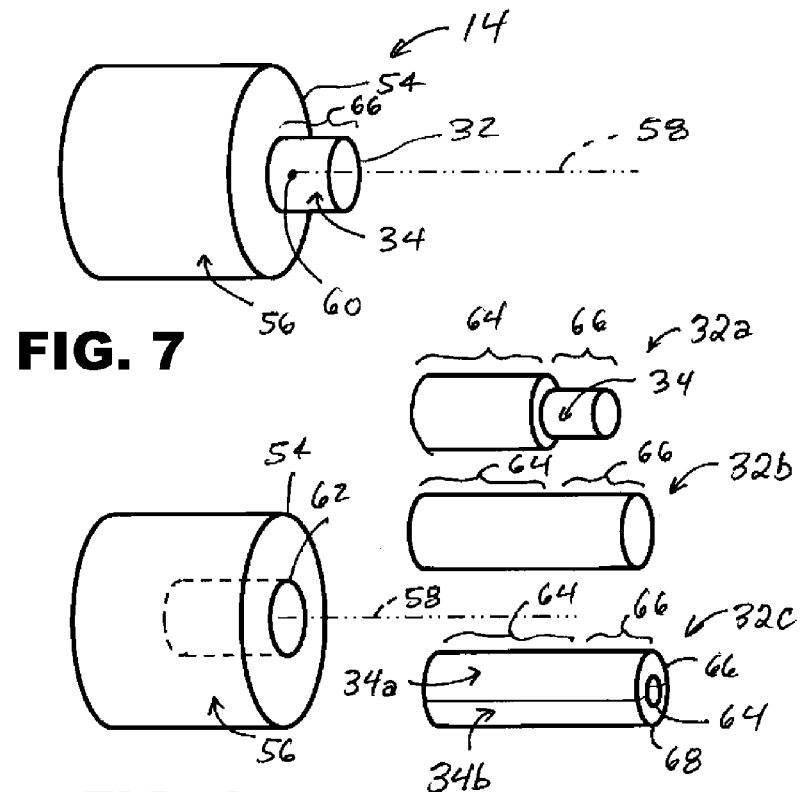
FIG. 7
FIG. 8
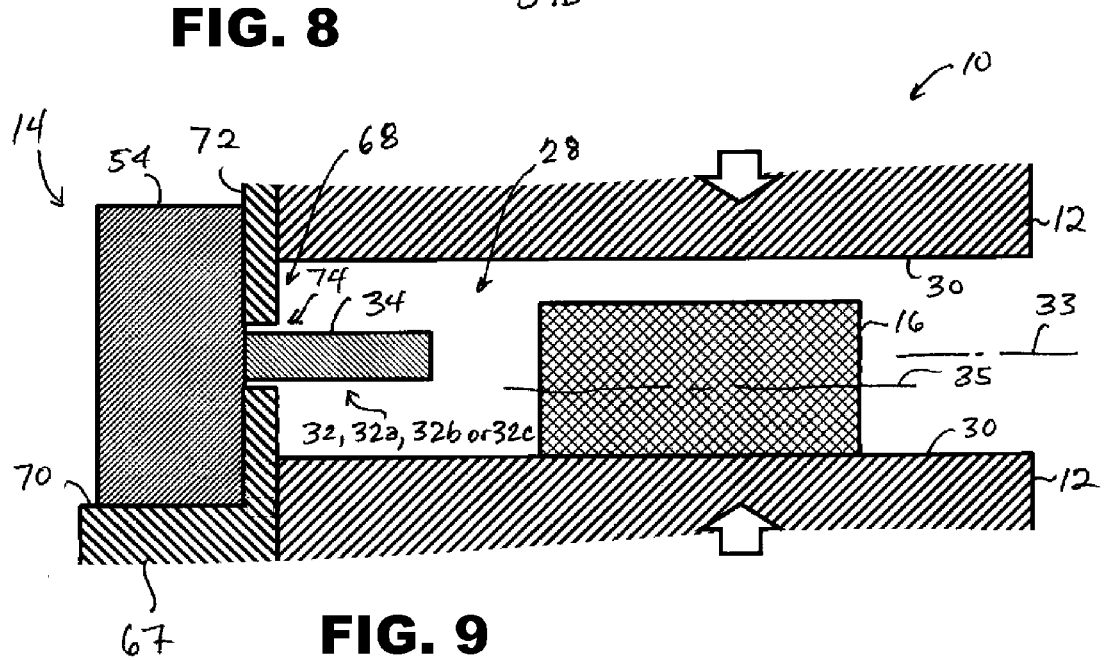
FIG. 9

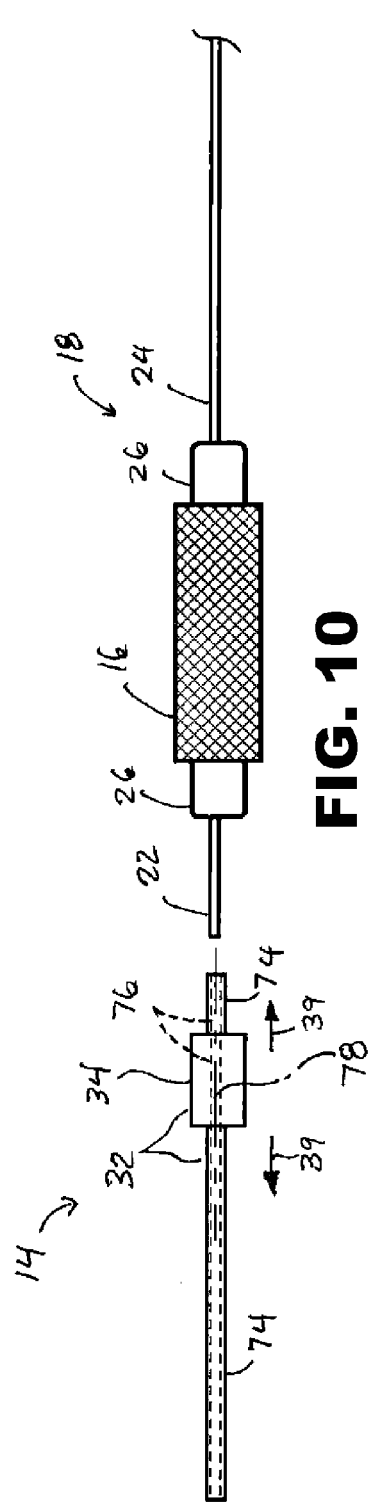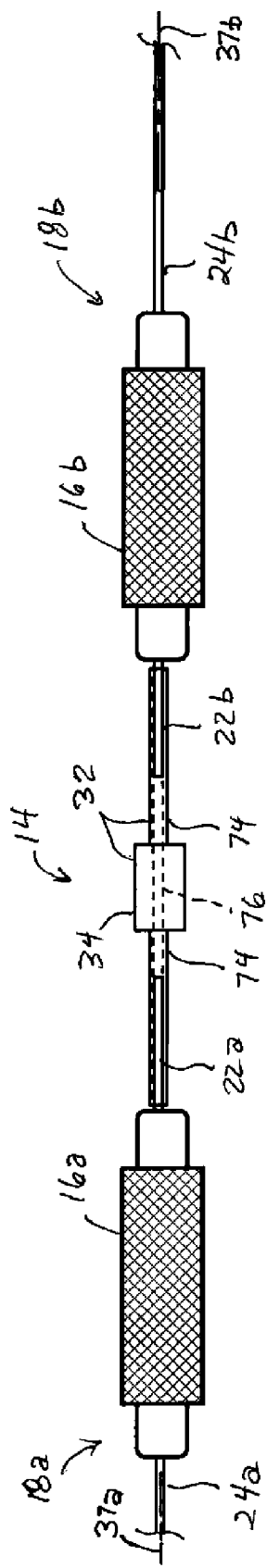

STENT CRIMPING TOOL INSERT, SYSTEM, AND METHOD

CROSS-REFERENCE TO RELATED APPLICATION

This application is a divisional application Ser. No. 13/840,185, filed Mar. 15, 2013, now U.S. Pat. No. 9,125,763, which application is hereby incorporated by reference.

FIELD OF THE INVENTION

This invention relates generally to devices for manufacturing stents, and more particularly to a crimping tool insert, system, and method for crimping a stent.

BACKGROUND

Stents are implanted permanently or temporarily in patients to treat a variety of medical conditions. Prior to implantation, stents are often radially collapsed or crimped to a small diameter to allow the stent to be delivered through small passageways, such as a blood vessel or other anatomical lumen. Stents are crimped onto and delivered using a catheter. After the stent reaches the location to be treated in the patient, the stent is expanded or allowed to expand.

Crimping of the stent may result in damage. Tools used to crimp stents can be set or preprogrammed to crimp the stent to a preselected diameter, or can be set or preprogrammed to apply a maximum force. The stent may still be over-crimped even when the stent crimping tool is properly set or programmed. Over-crimping refers to crimping of a particular stent to a diameter that is smaller than what is desired for that stent. Over-crimping can impose undue strain on the struts of the stent. Excessive strain may lead to cracking of stent struts during stent crimping or expansion, or may otherwise affect the ability of the stent to expand. Because stents can be extremely small and intricate, even the slightest variation in crimping can have an adverse effect. Polymeric stents can be particularly sensitive to over-crimping, although metal stents can also be affected by over-crimping.

Over-crimping can be the result of one or a combination of factors, including mechanical variations in the stent crimping tool, variances (such as material thickness variances) in the production of the stent and/or catheter, and environmental conditions that effect the physical condition of the stent crimping tool, stent and/or catheter.

Accordingly, there is a need for a stent crimping tool insert, system, and method that prevents over-crimping.

SUMMARY OF THE INVENTION

Briefly and in general terms, the present invention is directed to a stent crimping tool insert, stent crimping system, and stent crimping method.

In aspects of the present invention, a stent crimping tool insert comprises a core body configured for insertion into and removal from within a crimping chamber of a stent crimping tool. The core body has a core surface configured to withstand a compressive force without a reduction in diameter of the core surface.

In other aspects, the core body includes a first half-pipe and a second half-pipe movable relative to the first half-pipe, a first portion of the core surface is disposed on the first half-pipe, and a second portion of the core surface is disposed on the second half-pipe.

In other aspects, the first half-pipe is configured to engage onto and disengage from the second half-pipe, wherein when the first half-pipe is engaged onto the second half-pipe, the first half-pipe and the second half-pipe form a catheter passageway through the center of the core body.

In other aspects, the first half-pipe comprises a hinge attached to the second half-pipe.

In other aspects, the first half-pipe and the second half-pipe are magnetically attracted to each other.

In other aspects, the stent crimping tool insert further comprises a support member, wherein the first half-pipe and the second half-pipe are attached to and protrude from the support member.

In other aspects, the first half-pipe and the second half-pipe are configured to detach from and reattach to the support member.

In other aspects, the support member includes a cylindrical outer surface, the cylindrical outer surface and the first portion of the core surface are concentric, and the cylindrical outer surface and the second portion of the core surface are concentric.

In other aspects, the stent crimping tool insert further comprises a support member having a cylindrical outer surface, wherein the core body is attached to and protrudes from the support member at a point on a central axis of the cylindrical outer surface.

In other aspects, the core surface of the core body and the cylindrical outer surface of the support member are concentric.

In other aspects, the core body is configured to detach from and reattach to the support member.

In other aspects, the core body comprises a sheath having a catheter passageway extending through the sheath, and the catheter passageway is parallel to and centered on a central axis of the core surface of the core body.

In other aspects, the sheath is configured to attach to and detach from a catheter.

In aspects of the present invention, a stent crimping system comprises a stent crimping tool, and the stent crimping tool insert of any one of the above-described aspects.

In other aspects, the system further comprises a catheter and a stent carried on the catheter, wherein the stent crimping tool is configured to crimp the stent onto the catheter in a crimping chamber of the stent crimping tool, and the stent crimping tool insert is configured to resist movement of a crimping surface of the stent crimping tool within the crimping chamber and is configured to stop crimping of the stent by the crimping surface.

In aspects of the present invention, a stent crimping system comprises a stent crimping tool comprising a crimping chamber and crimping surfaces disposed around the crimping chamber, at least one of the crimping surfaces configured to move inward toward another one of the crimping surfaces, the inward movement causing a decrease in size of the crimping chamber. The system further comprises a stent crimping tool insert comprising a core body, the core body configured for insertion into and removal from within the crimping chamber, the core body having a core surface configured to stop the inward movement of the at least one crimping surface.

In other aspects, the core body is configured to withstand a compressive force from the crimping surfaces without a change in diameter of the core body.

In other aspects, the compressive force is greater than 1 pound.

In other aspects, the system further comprises a catheter and a stent carried on a catheter, wherein the stent crimping surfaces are configured to crimp the stent onto the catheter, and the stent crimping tool insert is configured to resist the inward movement of the at least one crimping surface and is configured to stop crimping of the stent by the crimping surfaces.

In other aspects, the system further comprises an insert holder disposed outside of the crimping chamber, the insert holder configured to carry the stent crimping tool insert at a position centered within the crimping chamber.

In aspects of the present invention, a stent crimping method comprises inserting a stent within a crimping chamber of a stent crimping tool, the stent having a starting diameter, the stent crimping tool having a crimping surface for crimping the stent. The method further comprises moving the crimping surface of the stent crimping tool, the movement of the crimping surface causing the stent to be crimped to a crimped diameter less than the starting diameter, wherein when the stent reaches the crimped diameter, a stent crimping tool insert within the crimping chamber resists or stops the movement of the crimping surface.

In other aspects, the method further comprises inserting the stent crimping tool insert into the crimping chamber before or during the movement of the crimping surface.

In other aspects, the method further comprises removing the stent crimping tool insert from within the crimping chamber after the stent reaches the crimped diameter.

In other aspects, the method further comprises coupling the stent crimping tool insert to the stent before or after the inserting of the stent within the crimping chamber.

In other aspects, the stent is carried on a catheter and the coupling of the stent crimping tool insert to the stent comprises mounting the stent crimping tool insert on the catheter.

In other aspects, the mounting of the stent crimping tool insert on the catheter comprises sliding the catheter into a catheter passageway inside the stent crimping tool insert.

In other aspects, the stent crimping tool insert comprises a first member and a second member configured to engage and disengage the first member, and the mounting of the stent crimping tool insert on the catheter comprises engaging the first member onto the second member while the catheter is disposed between the first member and the second member.

In other aspects, the method further comprises removing the stent crimping tool insert from the catheter after the stent reaches the crimped diameter.

In other aspects, the crimped diameter of the stent is preselected to be the diameter of the stent during any of sterilization of the stent while the stent is crimped on the catheter, packaging of the stent while the stent is crimped on the catheter, and percutaneous delivery of the stent while the stent is crimped on the catheter.

The features and advantages of the invention will be more readily understood from the following detailed description which should be read in conjunction with the accompanying drawings.

INCORPORATION BY REFERENCE

All publications, patent applications, and patents mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIGS. 7 and 8 are three-dimensional diagrams showing an exemplary stent crimping tool insert for use in the stent crimping systems of FIGS. 1-6 and 9.

FIG. 9 is a cross-section view showing an exemplary stent crimping system in which an exemplary stent crimping tool insert is carried on an exemplary insert holder.

FIGS. 10 and 11 are plan views showing an exemplary stent crimping tool insert coupled to one or more exemplary catheters.

DETAILED DESCRIPTION OF THE INVENTION

Figure 1:
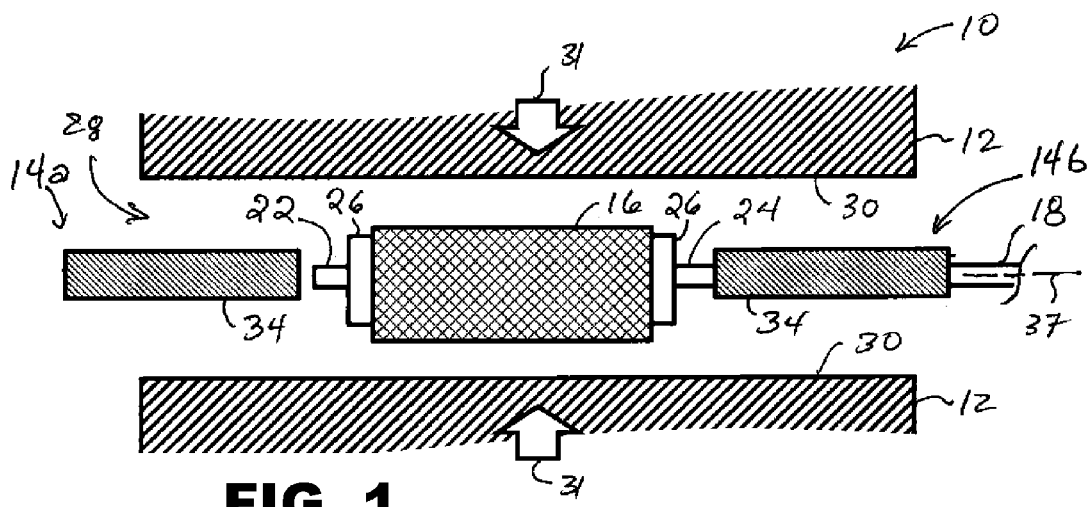
FIGS. 1-3 are cross-section views showing a sequence of operating an exemplary stent crimping system.

Referring now in more detail to the exemplary drawings for purposes of illustrating embodiments of the invention, wherein like reference numerals designate corresponding or like elements among the several views, there is shown in FIG. 1 stent crimping system 10 comprising stent crimping tool 12 and stent crimping tool inserts 14. Stent crimping tool 12 is configured to crimp a stent to a smaller size. Stent crimping tool inserts 14 are configured to prevent stent crimping tool 12 from crimping a stent to a size or diameter smaller than what is desired.

Figure 2:
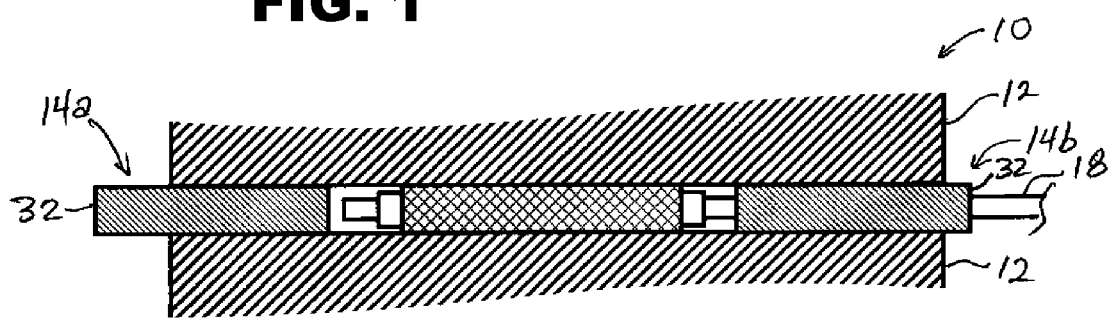
Figure 3:
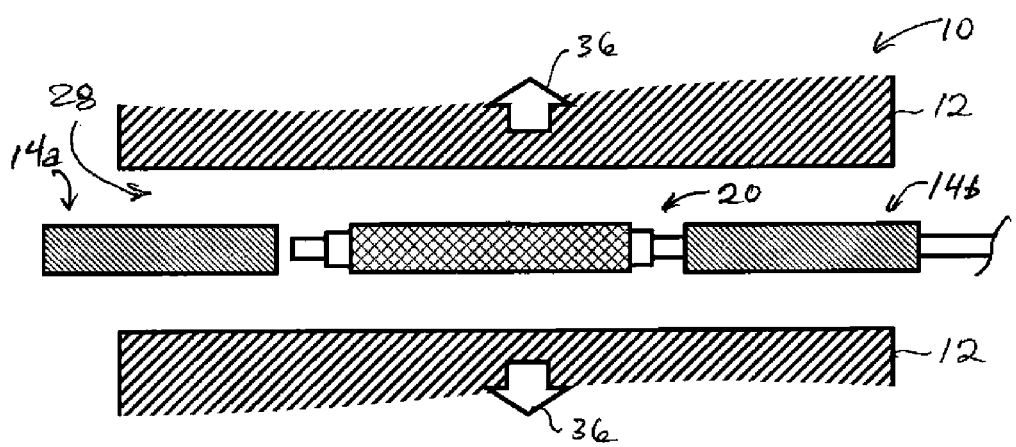

As shown in FIGS. 1-3, stent crimping tool 12 can be configured to crimp stent 16 onto catheter 18 to form stent-catheter assembly 20 (FIG. 3). In FIG. 1, stent 16, catheter 18, and stent crimping tool inserts 14 are placed in stent crimping tool 12. Stent 16 has an initial diameter. In FIG. 2, stent 16 is crimped by stent crimping tool 12 while stent crimping tool inserts 14 remain inside crimping tool 12 to prevent the possibility of over-crimping. Stent crimping tool insert 14 resists or stops the movement of crimping surfaces of crimping tool 12. In FIG. 3, stent crimping tool 12 releases stent 16, which is now at a crimped diameter that is smaller than the initial diameter.

In FIGS. 1-3, catheter 18 is a balloon catheter which includes distal catheter segment 22, proximal catheter segment 24, and inflatable balloon 26 connected to and disposed between the proximal and distal catheter segments. Initially, stent 16 is carried loosely on balloon 26, as shown in FIG. 1. Stent crimping tool 12 is configured to crimp stent 16 onto balloon 26 so that the stent remains secured on the balloon until the stent is deployed in a patient.

Stent crimping tool 12 includes crimping chamber 28 and crimping surfaces 30 disposed around the crimping chamber. At least one crimping surface 30 is configured to move inward toward the other crimping surface 30. The inward movement causes a decrease in the size of crimping chamber 28. Inward movement of crimping surfaces 30 can be accomplished by manual manipulation by a user of stent crimping tool 12 or by an electromechanical motor operatively coupled to crimping surfaces 30. In the illustrated embodiment, all crimping surfaces 30 are configured to move inward toward each other in the direction of arrows 31. Although two crimping surfaces 30 are illustrated in the cross-section views of FIGS. 1 to 3, it should be understood that stent crimping tool 12 may have any number of crimping surfaces 30 for simultaneously compressing stent 16 in multiple directions. As one or more stent crimping surfaces 30 move inward, they apply radially compressive force on the outer surface of stent 16.

As shown in FIG. 2, as one or more crimping surfaces 30 move inward, they may make contact with and bear upon core body 32 of crimping tool inserts 14 located within crimping chamber 28. Core body 32 is configured to resist inward movement of crimping surfaces 30 and limit the extent to which stent 16 is crimped. Core body 32 has cylindrical core surface 34 which, in cross-section, forms a circle having a preselected diameter. The preselected diameter of cylindrical core surface 34 may be selected based on the minimum outer diameter of stent 16 that is desired after crimping. The preselected diameter may correspond to the minimum outer diameter of stent 16 that is desired after crimping.

In other embodiments, the cross-section of cylindrical core surface 34 can have shapes other than a circle. The cross-sectional shape of cylindrical core surface 34 can vary depending on the configuration of crimping surfaces 30 of stent crimping tool 12. Examples of other cross-section shapes for cylindrical core surface 34 include without limitation octagon, square, and other polygons having flat sides. The number of flat sides can correspond to the number of crimping surfaces of the stent crimping tool. The preselected diameter of cylindrical core surface 34 can be in the range from 1 mm to 6 mm, and more narrowly 2 mm to 4 mm. It is to be understood that other preselected diameters may be implemented based on the desired minimum outer diameter of stent 16. For a cylindrical core surface having a polygon cross-section shape, the preselected diameter refers to that of a circle inscribed within the polygon shape.

As shown in FIG. 3, stent 16 is released by stent crimping tool 12 when crimping surfaces move outward in the direction of arrows 36. Upon release, stent 16 retains a crimped diameter that is smaller than its initial diameter shown in FIG. 1. Thereafter, stent-catheter assembly 20 is removed from crimping chamber 28. Stent crimping tool inserts 14 may optionally be removed from crimping chamber 28 before, during, or after withdrawal of stent-catheter assembly 20 from crimping chamber 28.

In FIGS. 1-3, two stent crimping tool inserts 14 are used to limit inward movement of crimping surfaces 30. One stent crimping tool insert 14a is positioned within crimping chamber 28 at a position distal to and adjacent to catheter distal segment 22. Another stent crimping tool insert 14b is positioned within crimping chamber 28 at a position around catheter proximal segment 24. Proximal stent crimping tool insert 14b can have core body 32 that is hollow with an internal cavity configured to receive catheter 18. Distal stent crimping tool insert 14a can have core body 32 that is solid in the sense that core body 32 has no internal cavity.

In other embodiments, only a single stent crimping tool insert 14 is positioned within crimping chamber 28. The single stent crimping tool insert 14 can be placed distal to and adjacent to catheter distal segment 22, or placed around catheter proximal segment 24.

Cylindrical core surface 34 of crimping tool insert 14 can be made of aluminum, stainless steel, nylon, or polycarbonate. Core body 32 can be made of aluminum, stainless steel, nylon, or polycarbonate. Core body 32 and cylindrical core surface 34 can be made of a biocompatible material. Core body 32 and cylindrical core surface 34 can be rigid and made of a non-compliant material. Core body 32 and cylindrical core surface 34 can be made of other materials.

In some embodiments, cylindrical core surface 34 is configured to withstand a compressive force within the force range of 1 pound (lb) to 400 lb without a reduction in the preselected diameter, and more narrowly within the force range of 1 lb to 350 lb without a reduction in its preselected diameter. The numerical range can be implemented by selection of the material and construction method for core body 32 and cylindrical core surface 34. The numerical range can be based on the expected force to be applied by crimping surfaces 30. For example, stent crimping tool 12 can be mechanically limited and/or preprogrammed to apply a force no greater than a maximum compressive force (for example, 1 lb), in which case cylindrical core surface 34 is configured to withstand a compressive force greater than the maximum compressive force of stent crimping tool 12 (for example, greater than 1 lb). In some embodiments, the core body is configured to withstand a compressive force (for example, greater than 1 lb, greater than 2 lb, greater than 5 lb, greater than 10 lb, or greater than 50 lb) from the crimping surfaces without a change in diameter of the core body.

Figure 4:
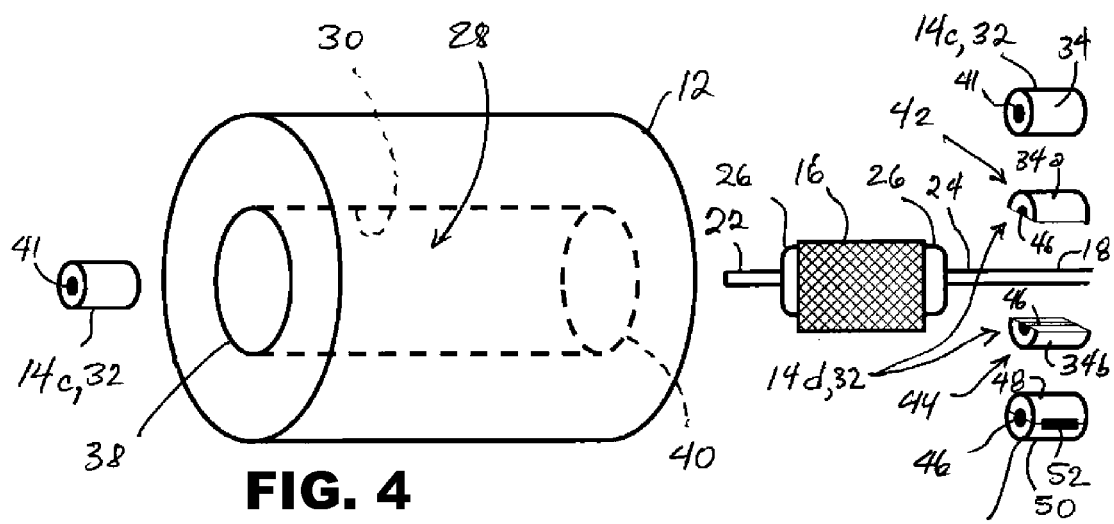
FIGS. 4-5 are three-dimensional diagrams showing a sequence of operating an exemplary stent crimping system.
Figure 5:
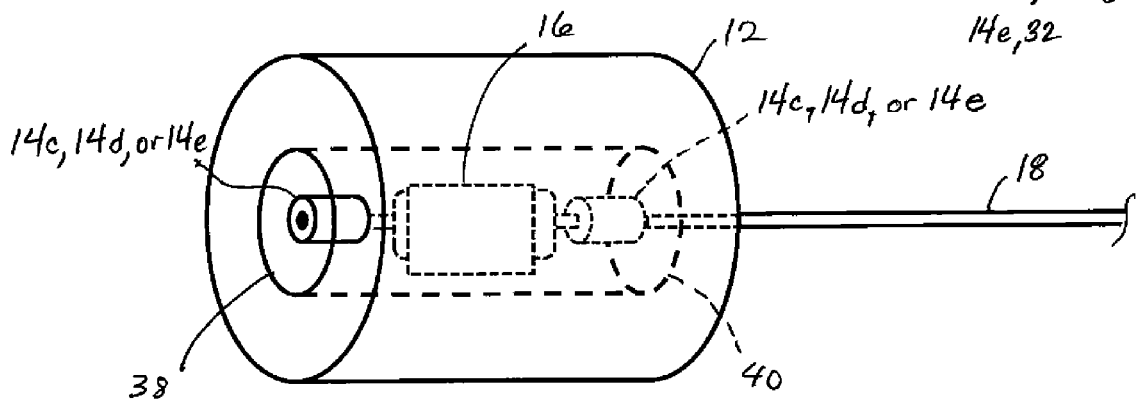
Figure 6:
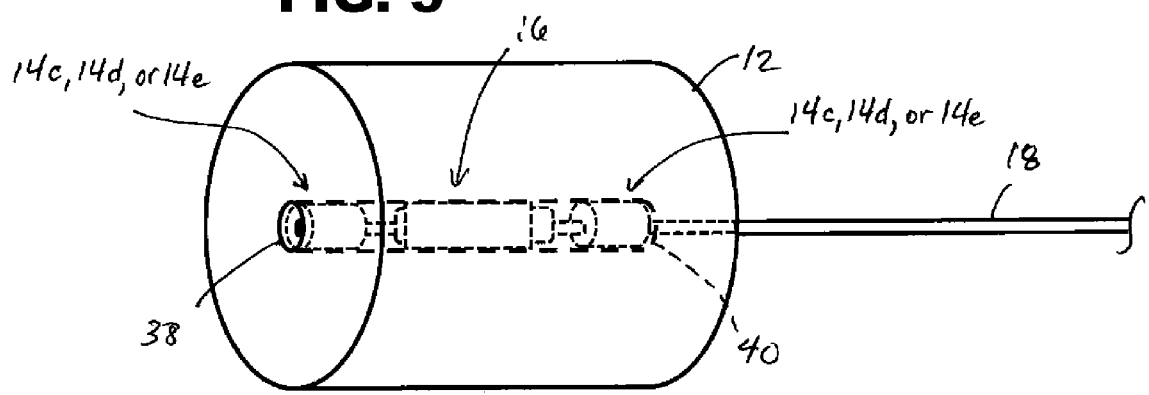

FIGS. 4-6 show a method of crimping a stent. Catheter 18 is inserted into the central lumen of stent 16 such that stent 16 is disposed around balloon 26, as shown in FIG. 4. Next, catheter 18 and stent 16 are inserted into crimping chamber 28 as shown in FIG. 5. Next, stent crimping tool 12 crimps stent 16 tightly onto balloon 26 as shown in FIG. 6.

Prior to crimping, stent crimping tool 12 is programmed to reduce crimping chamber 28 to a fixed diameter. The fixed diameter is selected to provide sufficient crimping that will achieve the desired stent crimped diameter and retention on catheter 18. The resistance of fully crimped stent 16 and underlying balloon 26 may cause crimping chamber 28 to reduce to a diameter that may vary slightly for one lot batch of stents to another lot batch. In the event of lot-to-lot variation in stent 16 or balloon 26, crimping surfaces 30 may close down further than desired and over-crimp stent 16. One or more stent crimping tool inserts 14 are used to prevent over-crimping.

At any time before crimping of stent 16 (before FIG. 6), one or more stent crimping tool inserts 14 are inserted into distal end opening 38 and/or proximal end opening 40 of crimping chamber 28. Insertion can be accomplished by sliding crimping tool insert 14 over catheter 18 such that catheter proximal segment 24 enters a cavity within crimping tool insert 14, and/or sliding crimping tool insert 14 over catheter 18 such that catheter distal segment 22 enters a cavity within crimping tool insert 14. Insertion of any of stent crimping tool inserts 14 can be performed before or after catheter 18 is inserted into crimping chamber 28.

One or more stent crimping tool inserts 14 can be temporarily carried by catheter 18, so that insertion of catheter 18 into crimping chamber 28 and insertion of crimping tool insert 14 into crimping chamber 28 are performed simultaneously.

Crimping of stent 16 is accomplished by reducing the size of crimping chamber 28. Crimping surfaces 30, which serve as the interior wall of crimping chamber 28, are moved radially inward toward each other. As a result of the radially inward movement, crimping surfaces 30 apply a compressive force to stent 16 which reduces the diameter of stent 16.

After stent 16 is crimped, stent crimping tool 12 releases stent 16. Release is accomplished by enlarging the size of crimping chamber 28. Crimping surfaces 30 are moved radially outward to their original position in FIG. 4, which allows stent 16 and catheter 18 to be withdrawn out of crimping chamber 28.

At any time after crimping of stent 16 (after FIG. 6), one or more of the previously-inserted stent crimping tool inserts 14 are withdrawn out of crimping chamber 28. Withdrawal can be accomplished by sliding crimping tool insert 14 away from stent 16 such that crimping tool insert 14 separates from catheter distal segment 22, and/or sliding crimping tool insert 14 away from stent 16 such that crimping tool insert 14 separates from catheter proximal segment 24.

After stent 16 is removed from crimping chamber 28, stent 16 may be subjected to further steps. Examples of further processing include without limitation sterilization of the stent while the stent is crimped on the catheter, packaging of the stent while the stent is crimped on the catheter, and percutaneous delivery of the stent while the stent is crimped on the catheter. In some embodiments, the crimped diameter of stent 16 immediately after removal from crimping chamber 28 corresponds the diameter of stent 16 during any of said sterilization, packaging, and/or percutaneous delivery.

Returning to FIG. 4, crimping tool inserts 14 can have different configurations, any of which can be inserted into distal end opening 38 or proximal end opening 40 of crimping chamber 28. Crimping tool insert 14c has cavity 41 which serves as a catheter passageway. Cavity 41 is configured to receive catheter distal segment 22 and/or catheter proximal segment 24. Crimping tool insert 14c can be a unitary pipe structure. Cylindrical core surface 34 of crimping tool insert 14c has a circle cross-section. Other cross-section shapes (for example, polygon shapes) can be implemented, as previously described above.

Crimping tool insert 14d includes first half-pipe 42 and second half-pipe 44 that are detachable and movable from each other. A first portion 34a of the cylindrical core surface 34 is disposed on first half-pipe 42. A second portion 34b of the cylindrical core surface 34 is disposed on second half-pipe 44. First half-pipe 42 is configured to engage onto and disengage from second half-pipe 44. Each of first half-pipe 42 and second half-pipe 44 has groove 46 extending across the entire longitudinal length of the half-pipe. When first half-pipe 42 is engaged onto second half-pipe 44, the grooves join to form a linear catheter passageway through the center of crimping tool insert 14d.

In some embodiments, first half-pipe 42 and second half-pipe 44 are magnetically attracted to each other. Any one or both of first half-pipe 42 and second half-pipe 44 may contain a magnet. In use, a user pulls both half-pipes apart and places catheter 18 between the two half-pipes. Prior to crimping of stent 16, the user closes crimping tool insert 14d onto catheter 18 by bringing the two half-pipes into contact with each other while catheter 18 is disposed within grooves 46 of the half-pipes. Magnetic attraction between the half-pipes keeps crimping tool insert 14e in place during stent crimping. After crimping of stent 16, the user opens crimping tool insert 14d by pulling both half-pipes apart to allow catheter 18 to separate from crimping tool insert 14d.

In FIG. 4, crimping tool insert 14e includes first half-pipe 48 having a hinge 52 attached to second half-pipe 50. In use, a user pivots the half-pipes apart by hinge 52. Prior to crimping of stent 16, the user closes crimping tool insert 14e onto catheter 18 by pivoting the two half-pipes into contact with each other while catheter 18 is disposed within grooves 46 of the half-pipes. A mechanical latch or magnet between the half-pipes keeps crimping tool insert 14e in place during stent crimping. After crimping of stent 16, the user opens crimping tool insert 14e by pivoting the half-pipes apart to allow catheter 18 to separate from crimping tool insert 14e.

In FIGS. 1-6, core body 32 forms the entirety of stent crimping tool insert 14. In other embodiments, core body 32 is configured differently that what is shown in FIGS. 1-6, and stent crimping tool insert 14 may include other structures coupled to core body 32.

As shown in FIGS. 7-9, crimping tool insert 14 may include support member 54. Any core body 32 in FIGS. 1-6 may be carried by support member 54 as shown in FIGS. 7-9. Support member 54 facilitates placement of core body 32 at the desired location within crimping chamber 28 of stent crimping tool 12.

In FIGS. 7-9, support member 54 has a circular shape with curved side walls and flat end walls. In other embodiments, the support member can have other shapes and can have a flat side wall. For example, the support member can be a rectangular block.

As shown in FIG. 7, support member 54 includes cylindrical outer surface 56. Core body 32 includes cylindrical core surface 34. Each of cylindrical outer surface 56 and cylindrical core surface 34 has a circle cross-section shape, although other cross-section shapes (for example, polygon shapes) may be implemented as previously described above. For example, cylindrical core surface 34 can have a polygon cross-section. Core body 32 has a smaller outer diameter than that of support member 54. Cylindrical outer surface 56 has central axis 58. Core body 32 protrudes out from support member 54 at a point 60 on central axis 58. Cylindrical outer surface 56 and cylindrical core surface 34 are concentric.

Optionally, core body 32 and support member 54 are a single unitary structure. Core body 32 and support member 54 are integrally formed with each other. Various manufacturing process including without limitation, injection molding, milling, and/or other machining operations can be used to make a single unitary structure with core body 32 and support member 54.

As shown in FIG. 8, core body 32 and support member 54 can be distinct structures capable of being assembled and disassembled. Support member 54 includes hole 62 configured to receive core body 32. Hole 62 may extend through the entire longitudinal length of support member 54. The same support member 54 can be used to hold any one of a variety of core bodies 32a, 32b, 32c which can vary by diameter and functional characteristics. Any of core bodies 32a, 32b, and 32c can be attached and subsequently detached from support member 54. For example, core body 32a can be inserted into support member 54, and then exchanged with core body 32b or 32c. Core bodies 32a, 32b, and 32c each include base segment 64 and protruding segment 66. Base segment is retained inside hole 62. Retention can be accomplished with a press fit, friction fit, screw-type thread, and/or other means of securement. Protruding segment 66 protrudes out from support member 54, as shown in FIG. 7.

When any of core body 32a, 32b, or 32c is inserted in hole 62, cylindrical core surface 34 of the core body is concentric with cylindrical outer surface 56 of support member 54. Cylindrical core surface 34 is disposed on protruding segment 66 and has a preselected outer diameter. The preselected diameter of cylindrical core surface 34 may be selected based on the minimum outer diameter of stent 16 that is desired as a result of crimping. The preselected diameter of cylindrical core surface 34 may be equivalent to the minimum outer diameter of stent 16 that is desired as a result of crimping. Thus, different core bodies 32a, 32b, and 32c can be selected and used depending on the desired minimum outer diameter of stent 16. For example, first core body 32a having a diameter suitable for one batch of stents can be replaced with second core body 32b having a different diameter suitable for the next batch of stents. As a further example, core body 32c has linear catheter passageway 64 extending through the entire longitudinal length of core body 32c. Core body 32c can be inserted into support member 54 when it is desired to have the core body centered on and carried by catheter 18, as shown in FIGS. 5 and 6.

In some embodiments, core body 32c has the same configuration as that of stent crimping tool insert 14c, 14d, or 14e (FIG. 4). Core body 32c may include two identical half-pipe members 66, 68 configured to engage and disengage from each other. Any one or both of half-pipes 66, 68 may optionally include an embedded magnet or a hinge. A first portion 34a of the cylindrical core surface is disposed on first half-pipe 66. A second portion 34b of the cylindrical core surface is disposed on second half-pipe 68. When core body 32c is inserted into hole 62, first portion 34a and second portion 34b are concentric with cylindrical outer surface 56 of support member 54.

FIG. 9 shows support member 54 in use with stent crimping tool 12. Insert holder 67 is attached to stent crimping tool 12. Insert holder 67 is disposed outside of crimping chamber 28 of stent crimping tool 12. Insert holder 67 is disposed adjacent to an end opening 68 of crimping chamber 28. Insert holder 67 includes support surface 70 configured to carry support member 54 such that core body 32 is at a location in crimping chamber 28 toward which crimping surfaces 30 converge during crimping of stent 16. Support surface 70 is configured to carry support member 54 such that core body 32 is centered vertically within crimping chamber 28.

In the illustrated embodiment, crimping surfaces 30 converge toward convergence axis 33 during crimping. Support surface 70 is configured to carry support member 54 such that core body 32 is centered on convergence axis 33.

In other embodiments, insert holder 67 is configured to carry support member 54 such that core body 32 is centered on central axis 35 of stent 16 (FIG. 9) or centered on central axis 37 of catheter 18 (FIG. 1).

Insert holder 67 includes stop wall 72 which partially covers end opening 68. Through-hole 74 extends through stop wall 72. Core body 32 extends through through-hole 74 when support member 54 is carried on support surface 70. Through-hole 74 has a diameter that is the same as or greater than that of core body 32. In the illustrated embodiment, the through-hole diameter is larger than that of core body 32 so that there is a gap between the peripheral edge of through-hole 74 and cylindrical core surface 34 of core body 32. The gap allows core body 32 to adjust position toward convergence axis 33 during crimping. Adjustment in position may be needed due to slight misalignment of insert holder 67 relative to crimping tool 12 or due to mechanical variations within crimping tool 12.

Support member 54 and/or insert holder 67 can be implemented with the devices and methods of FIGS. 1-6.

In FIG. 9, stent 16 is crimped by itself, without having been placed on a catheter. After such crimping, stent 16 may be placed on catheter 18 and crimped further in order to secure stent 16 onto catheter.

As shown in FIGS. 10 and 11, stent crimping tool insert 14 can be in the form of a stylet. In this form, core body 32 includes sheath 74 having linear catheter passageway 76 extending through the sheath. Sheath 74 is configured to attach to and detach from catheter 18. Catheter passageway 76 is parallel to and centered on central axis 78 of cylindrical core surface 34 of core body 32. Catheter passageway 76 is configured to receive catheter distal segment 22 and/or catheter proximal segment 24. Catheter passageway 76 allows core body 32 to be mounted on catheter 18.

Sheath 74 may be a flexible or rigid tube. Sheath 74 can be made of the same or different material as cylindrical core surface 34. Cylindrical core surface 34 is configured to withstand a compressive force within a selected force range, as previously described above, without a reduction in diameter of the cylindrical core surface. Sheath 74 does not need to withstand compressive forces of stent crimping tool 12.

In some embodiments, cylindrical core surface 34 can slide axially on sheath 74 in the direction of arrows 39. In alternative embodiments, cylindrical core surface 34 is permanently affixed to a single location on sheath 74.

Referring to FIG. 10, stent crimping tool insert 14 (referred to as a stylet) is mounted to catheter distal segment 22. Stent 16 is crimped by stent crimping tool 12 while the stylet is mounted on catheter distal segment 22. In some embodiments, a first stylet is mounted on a distal segment of a first catheter carrying a first stent. A second stylet is mounted on a distal segment of a second catheter carrying a second stent. Both catheters are placed into stent crimping tool 12 to allow simultaneous crimping of both stents. During crimping, the cylindrical core surfaces of both styles prevent crimping tool 12 from crimping the stents to a diameter smaller than what is desired. The catheters can be oriented within stent crimping tool 12 such that the distal segment of the first catheter faces toward the distal segment of the second catheter. Optionally, the catheters can be oriented within stent crimping tool 12 such that they are coaxial in the sense that their respective longitudinal axes are coincident. Optionally, there can be a longitudinal gap between the two stylets within stent crimping tool 12 during stent crimping.

As shown in FIG. 11, a single stent crimping tool insert 14 can be mounted on two catheters 18a, 18b. First stent 16a can be carried on first catheter 18a inserted into linear catheter passageway 76 of core body 32. Second stent 16b can be carried on second catheter 18b inserted into catheter passageway 76 of core body 32. Thereafter, crimping tool insert 14 and both stents 16a, 16b can be inserted into crimping chamber 28 of stent crimping tool 12. Next, both stents 16a, 16b can be crimped simultaneously in crimping chamber 28. During crimping, cylindrical core surface 34 prevents crimping tool 12 from crimping stents 16a, 16b to a diameter smaller than what is desired.

In FIGS. 10 and 11, the longitudinal length of sheath 74 of stent crimping tool insert 14 can vary. The length of sheath 74 can be selected depending on the type of stent crimping tool, type of catheter, type of stent, and/or other factors.

Each of stent crimping tools 14 shown in FIGS. 10 and 11 are referred to as a stylet. A stylet can be used in conjunction with the stent crimping tool inserts 14a, 14b, 14c, 14d, 14e of FIGS. 1-9.

Before crimping of stent 16, a stylet is mounted to catheter distal segment 22, and any of the stent crimping tool insert in FIG. 1-9 can be mounted on the catheter proximal segment 24. Stent 16 can then be crimped onto balloon 26 with the stylet and any of the stent crimping tool insert in FIG. 1-9 mounted on catheter 18. During crimping, two separate cylindrical core surfaces prevent over-crimping by crimping tool 12.

As a variation of FIG. 11, a first stylet is mounted on distal segment 22a of first catheter 18a, and any of the stent crimping tools in FIG. 1-9 can be mounted on the proximal segment 24a of catheter 18a. A second stylet is mounted on distal segment 22a of second catheter 18b, and any of the stent crimping tools in FIG. 1-9 can be mounted on the proximal segment 24b of second catheter 18b. Both catheters 18a, 18b are placed into stent crimping tool 12 to allow simultaneous crimping of stents 16a, 16b. During crimping, four separate cylindrical core surfaces prevent over-crimping by crimping tool 12. Catheters 18a, 18b can be oriented within stent crimping tool 12 such that distal segment 22a faces distal segment 22b. Optionally, the catheters can be oriented within stent crimping tool 12 such that they are coaxial in the sense that their respective longitudinal central axes 37a, 37b are coincident. Optionally, there can be a longitudinal gap between the two stylets within stent crimping tool 12 during stent crimping.

Figure 12:
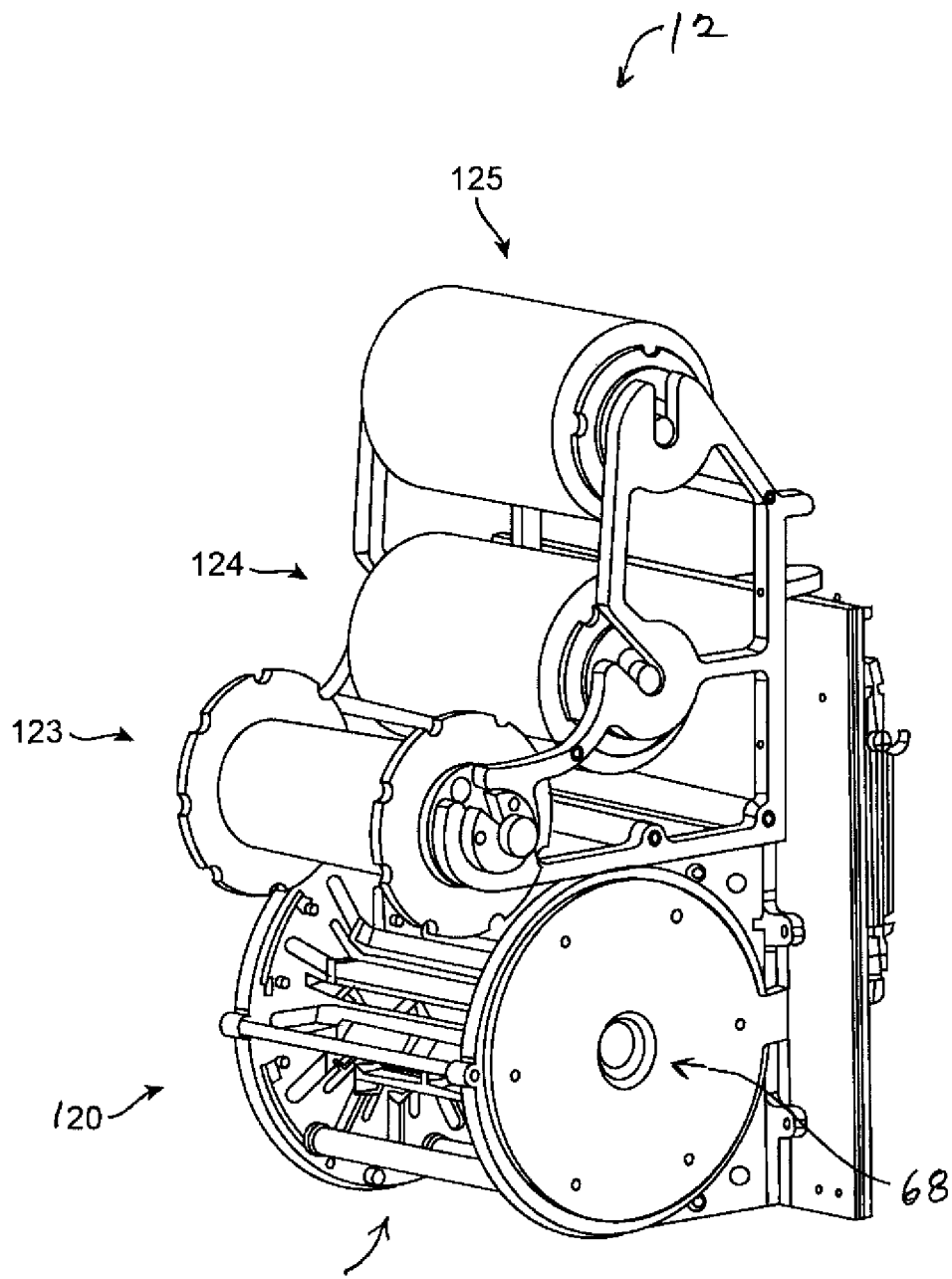
FIG. 12 is a perspective view showing an exemplary stent crimping tool.
Figure 13:
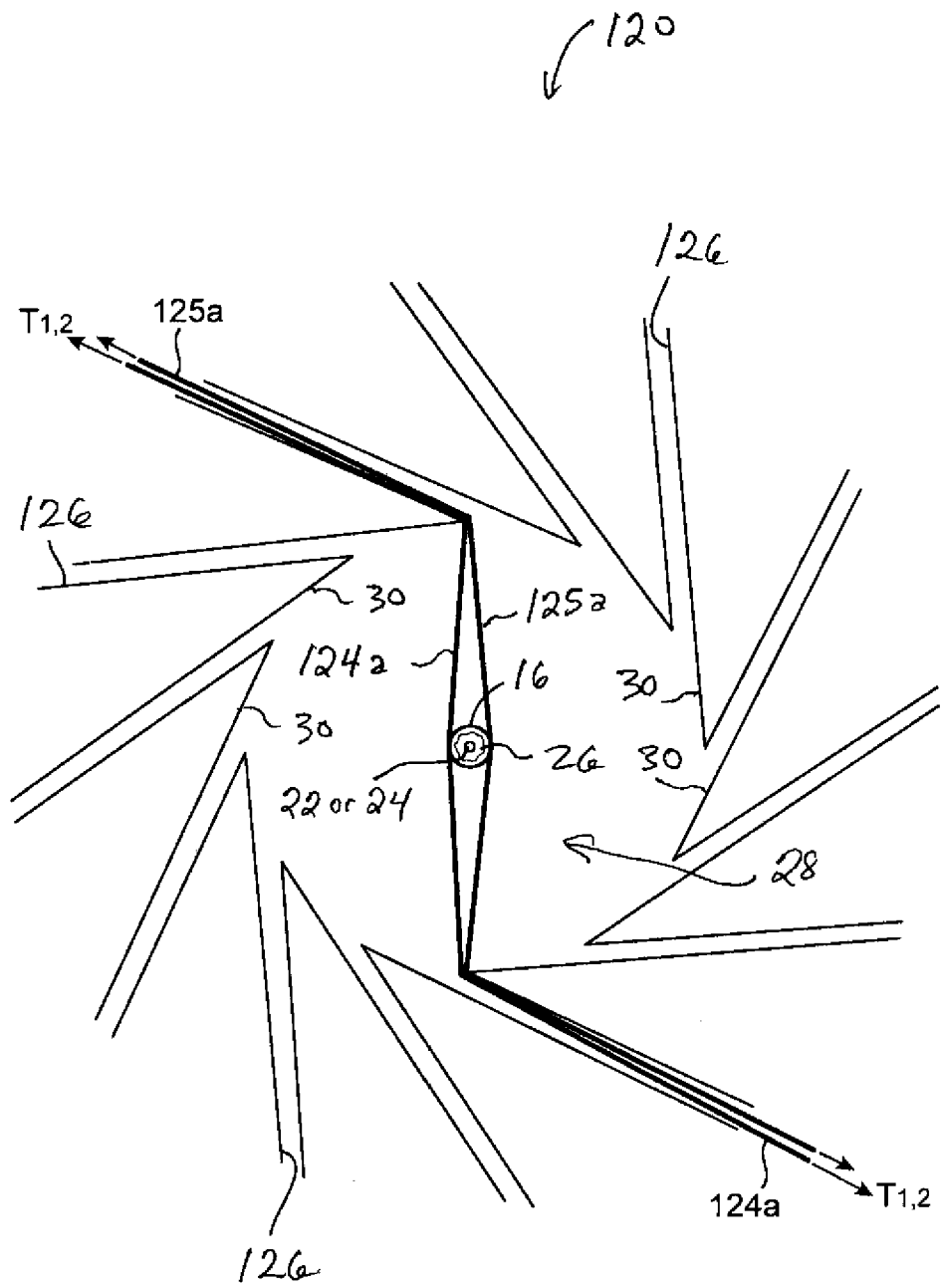
FIG. 13 is an end view showing a crimping chamber of the stent crimping tool of FIG. 12.

As shown in FIGS. 12 and 13, exemplary stent crimping tool 12 can be a film-headed crimper apparatus. In FIG. 12, stent crimping tool 12 includes three rolls 123, 124, 125 used to position clean sheets of non-stick material between a stent and crimping blades or wedges 126 within crimper head 120 prior to crimping. For example, upper roll 125 holds the sheet secured to a backing sheet. A first non-stick sheet material is separated from the backing sheet by a rotating mechanism within the crimper head 120. A second non-stick sheet material is dispensed from mid roll 124. After crimping, the first and second non-stick sheets are collected by the lower roll 123.

As an alternative to rollers 124, 125 dispensing non-stick sheets, the stent may be covered in a thin, compliant protective sheath before the stent is crimped by crimping wedges 126 within crimper head 120.

FIG. 13 shows positioning of first non-stick sheet material 125a and second first non-stick sheet material 124a relative to the crimping wedges 126 and stent 16 within iris-type crimping chamber 28 within crimper head 120. Iris-type crimping chamber 28 is shown in an enlarged state, and stent 16 is shown in an uncrimped state. Prior to crimping, sheets 124a, 125a are passed between two wedges 126 on opposite sides of the stent 16. Tension T1, T2 is applied to each of the sheets 124a, 125a to gather up excess sheet material as iris-type crimping chamber 28 is reduced in size via the converging wedges 126. Crimping surfaces 30 are the portions of wedges 126 exposed to stent 16. As wedges 126 converge, crimping surfaces 30 apply compressive force to stent 16. Before or while wedges 126 converge, stent crimping tool insert 14 is inserted into end opening 68 (FIG. 12) of iris-type crimping chamber 28. Core body 32 of stent crimping tool insert 14 would be located between sheets 124a, 125a. Stent crimping tool insert 14 prevents wedges 126 from crimping stents 16 to a diameter smaller than what is desired.

In some embodiments, iris-type crimping chamber 28 is used without sheets 124a, 125a, and wedges 126 may contact core body 32 of stent crimping tool insert 14 to prevent over-crimping of stent 16.

Stent crimping tool 12 can be any one of a variety of different tools known in the art for crimping stents, such as those described in U.S. Pub. Nos. 2008/0127707, 2009/0131920, 2010/0185207, 2012/0284986, and 2012/0010693.

Figure 14:
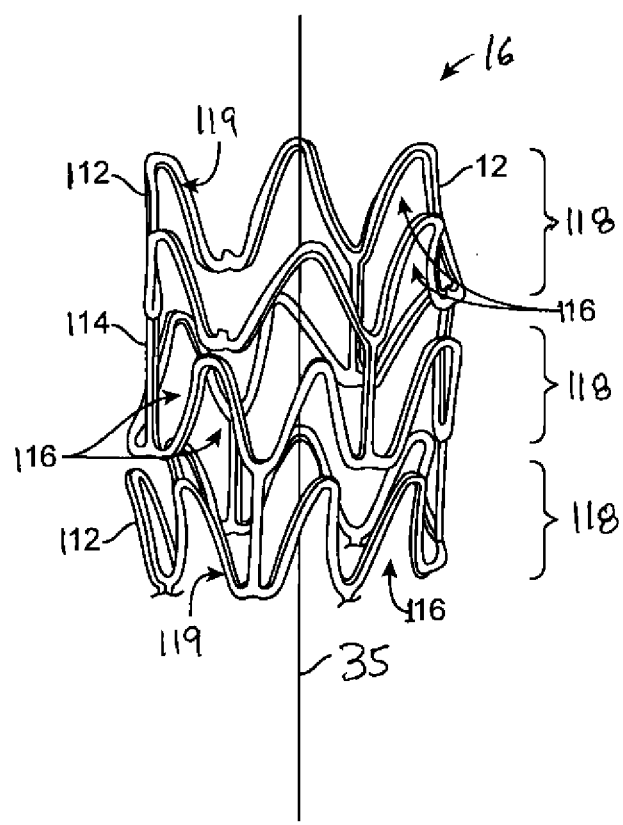
FIG. 14 is a perspective view showing an exemplary stent.

FIG. 14 shows an end segment of exemplary stent 16. Stent 16 has an overall body shape that is hollow and tubular. Stent 16 is configured for temporary or permanent implantation in a patient. Stent 16 may have a coating. The coating may include a drug. Stent 16 is shown in an uncrimped or expanded state. Stent 16 includes many interconnecting struts 112, 114 separated from each other by gaps 116. The struts 112, 114 form a tubular scaffold and can be made of any suitable material, such as a biocompatible metal or polymer. The material can be non-bioabsorbable or bioabsorbable. Struts 112 form series of rings 118. Rings 118 are connected to each other by struts 114. Struts 112 are configured to bend relative to each other at hinge areas 119 to allow the rings 118 to be crimped to a smaller diameter and expanded to a larger diameter. Struts 114 are configured to flex to allow the scaffold to bend along its longitudinal length, which facilities delivery through tortuous blood vessels and other anatomical lumen.

Stent 16 is configured to be crimped to a smaller diameter and expanded after crimping. Stent 16 can be any one of a variety of self-expanding stent or a balloon expandable stents known in the art. The variation in stent patterns is virtually unlimited. For example, stent 16 can have same structural configuration as, be made of the same materials as, or be identical to the stents described in U.S. Pat. Nos. 8,002,817; 5,569,295; and 5,514,154.

Catheter 18 can be any one of a variety of stent delivery devices known in the art. For example, catheter 18 can have same structural configuration as, be made of the same materials as, or be identical to the stent delivery devices described in the above-listed patents and in U.S. Pat. No. 6,626,933.

The stent crimping tool insert, stent crimping system, and stent crimping method of the present invention can be used in an individual step and in crimping methods described in U.S. Pub. Nos. 2009/0088829, 2010/0036478, and 2012/0010693.

Stent crimping tool insert 14 and/or insert holder 67 can be used in combination with the crimping tools described in the above-listed publications and patents.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:
1. A stent crimping method comprising:
  inserting a stent within a crimping chamber of a stent crimping tool, the stent having a starting diameter, the stent crimping tool having a crimping surface for crimping the stent;
  moving the crimping surface of the stent crimping tool, the movement of the crimping surface causing the stent to be crimped to a crimped diameter less than the starting diameter, wherein when the stent reaches the crimped diameter, a stent crimping tool insert within the crimping chamber resists or stops the movement of the crimping surface; and
  coupling the stent crimping tool insert to the stent before or after the inserting of the stent within the crimping chamber,
  wherein the stent is carried on a catheter and the coupling of the stent crimping tool insert to the stent comprises mounting the stent crimping tool insert on the catheter.
2. The stent crimping method of claim 1, further comprising inserting the stent crimping tool insert into the crimping chamber before or during the movement of the crimping surface.

3. The stent crimping method of claim 1, further comprising removing the stent crimping tool insert from within the crimping chamber after the stent reaches the crimped diameter.

4. The stent crimping method of claim 1, wherein the mounting of the stent crimping tool insert on the catheter comprises sliding the catheter into a catheter passageway inside the stent crimping tool insert.

5. The stent crimping method of claim 1, wherein the stent crimping tool insert comprises a first member and a second member configured to engage and disengage the first member, and the mounting of the stent crimping tool insert on the catheter comprises engaging the first member onto the second member while the catheter is disposed between the first member and the second member.

6. The stent crimping method of claim 1, further comprising removing the stent crimping tool insert from the catheter after the stent reaches the crimped diameter.

7. The stent crimping method of claim 1, wherein the crimped diameter of the stent is preselected to be the diameter of the stent during any of:
 sterilization of the stent while the stent is crimped on the catheter,
 packaging of the stent while the stent is crimped on the catheter, and
 percutaneous delivery of the stent while the stent is crimped on the catheter.

\* \* \* \* \*